United States Patent
Ochiai

(10) Patent No.: US 6,600,809 B1
(45) Date of Patent: Jul. 29, 2003

(54) NONDESTRUCTIVE INSPECTION APPARATUS

(75) Inventor: Yutaka Ochiai, Hamamatsu (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

(21) Appl. No.: 10/111,802

(22) PCT Filed: Oct. 27, 2000

(86) PCT No.: PCT/JP00/07561

§ 371 (c)(1),
(2), (4) Date: Apr. 29, 2002

(87) PCT Pub. No.: WO01/33920

PCT Pub. Date: May 10, 2001

(30) Foreign Application Priority Data

Oct. 29, 1999 (JP) .......................................... 11-309835

(51) Int. Cl.[7] ................................................ H05G 1/10
(52) U.S. Cl. ........................ 378/101; 378/136; 378/201
(58) Field of Search ................................ 378/136, 201, 378/101–113

(56) References Cited

U.S. PATENT DOCUMENTS 3,812,366 A * 5/1974 Gralenski .................... 378/101

FOREIGN PATENT DOCUMENTS

| JP | 58-14499 | 1/1983 |
|---|---|---|
| JP | 6-188092 | 7/1994 |
| JP | 8-162285 | 6/1996 |
| JP | 10-39097 | 2/1998 |
| JP | 10-503618 | 3/1998 |
| WO | WO 96/29723 | 9/1996 |

* cited by examiner

Primary Examiner—Craig E. Church
(74) Attorney, Agent, or Firm—Morgan, Lewis & Bockius LLP

(57) ABSTRACT

A nondestructive inspection apparatus with integrated power supply comprises a molded power supply section (14) having a resin-molded high voltage (e.g. 160 kV) generating section (15) secured to the base of a tubular section (2). The durability and handlability are improved by omitting a high voltage cable. Since the high voltage generating section (15) is confined in a molding resin, the degree of freedom in the arrangement of the high voltage generating section (15) within the mold is enhanced significantly. Furthermore, an X-ray generating unit (1) can be installed stably in the nondestructive inspection apparatus (70) by disposing the heavy molded power supply section (14) under a target (10).

4 Claims, 7 Drawing Sheets

NONDESTRUCTIVE INSPECTION APPARATUS

TECHNICAL FIELD

The present invention relates to a nondestructive inspection apparatus; and, in particular, to a nondestructive inspection apparatus utilizing an open type X-ray generating apparatus making it possible to replace a filament part, which is a consumable, upon vacuum aspiration by use of a pump.

BACKGROUND ART

An X-ray generating apparatus utilized in such a field has conventionally been known from Japanese Patent Application Laid-Open No. HEI 10-503618. In the X-ray generating apparatus disclosed in the above-mentioned publication, electron beams emitted from a cathode are focused onto a target by an electromagnetic action of a coil, whereby an X-ray beam is emitted from a target toward an object to be inspected. Here, since the X-ray generating apparatus operates at a very high voltage of 160 kV, it has a separate, large-size, high-voltage power unit which is connected to the X-ray generating apparatus by a high-tension cable.

Since the high-voltage power unit for driving the X-ray generating apparatus has a structure for generating a very high voltage of 100 kV to 300 kV, however, the high-tension cable for transmitting this voltage to the X-ray generating apparatus must become very thick (e.g., a diameter of 40 mm) and heavy. The handling of such a high-tension cable is required to be managed quite strictly. Namely, the degree of freedom in bending this high-tension cable is very low because of its high-tension characteristics and structure, whereby extreme caution must be taken to prevent disasters from occurring due to electric leakage upon connection to the X-ray generating apparatus, and periodical maintenance is necessary for preventing electric leakage from occurring from a connecting part, thus putting an excessive load on operators and users. In addition, the weight of high-tension cable has been a factor further enhancing the burden of operators.

When such an X-ray generating apparatus is placed in a nondestructive inspection apparatus, the high-tension cable has a very low degree of freedom in bending, whereby the X-ray generating apparatus will be placed under a suspending state in the nondestructive inspection apparatus if the high-tension cable is one extending from the lower part of the X-ray generating apparatus, thus yielding an unstable fixing state. Such a restriction results from the difficulty in traveling of the high-tension cable.

For overcoming the problem mentioned above, it is an object of the present invention, in particular, to provide an on destructive inspection apparatus which can stably place an open type X-ray generating apparatus making its filament part replaceable.

DISCLOSURE OF THE INVENTION

The nondestructive inspection apparatus of the present invention is a nondestructive inspection apparatus for irradiating an object to be inspected with an X-ray generated from an open type X-ray generating apparatus which irradiates a target with an electron emitted from an electron gun having a replaceable filament part so as to release the X-ray from the target, and capturing a state of the object to be inspected with an X-ray camera; the open type X-ray generating apparatus comprising a tubular portion, adapted to be vacuumed by a pump, having a coil part therewithin and an electron path surrounded by the coil part; and a mold power unit, secured to a proximal end side of the tubular portion, having a resin-molded high-voltage generating part; wherein the mold power unit is secured to a base plate while in a state where the target disposed on one end side of the tubular portion and the mold power unit disposed on the other end side of the tubular portion are located on the upper and lower sides, respectively.

This nondestructive inspection apparatus utilizes vacuum aspiration effected by the pump, so as to make it possible to replace the filament part, which is a consumable, thereby improving the maintenance. Such an apparatus is required to have not only durability but also easiness in handling. Hence, for eliminating the high-tension cable in order to improve the handling, a mold power unit in which a high-voltage generating part attaining a high voltage (e.g., 160 kV) is molded with a resin is employed, whereas this mold power unit is secured to the proximal end side of the tubular portion, whereby an apparatus of a type integrated with a power supply is realized. Since the high-voltage generating part is confined within the resin mold as such, the degree of freedom in configuration of the high-voltage generating portion improves remarkably. Also, since the heavy mold power unit and the target are located on the lower and upper sides, respectively, the X-ray generating apparatus can be placed in the nondestructive inspection apparatus while in a stable state. In addition, since the conventional necessity for the high-tension cable is eliminated, the heavy mold power unit can be secured onto the base plate of the nondestructive inspection apparatus, whereby the X-ray generating apparatus can further be stabilized.

BEST MODE FOR CARRYING OUT THE INVENTION

In the following, a preferred embodiment of the nondestructive inspection apparatus in accordance with the present invention will be explained in detail with reference to the drawings.

Figure 1:
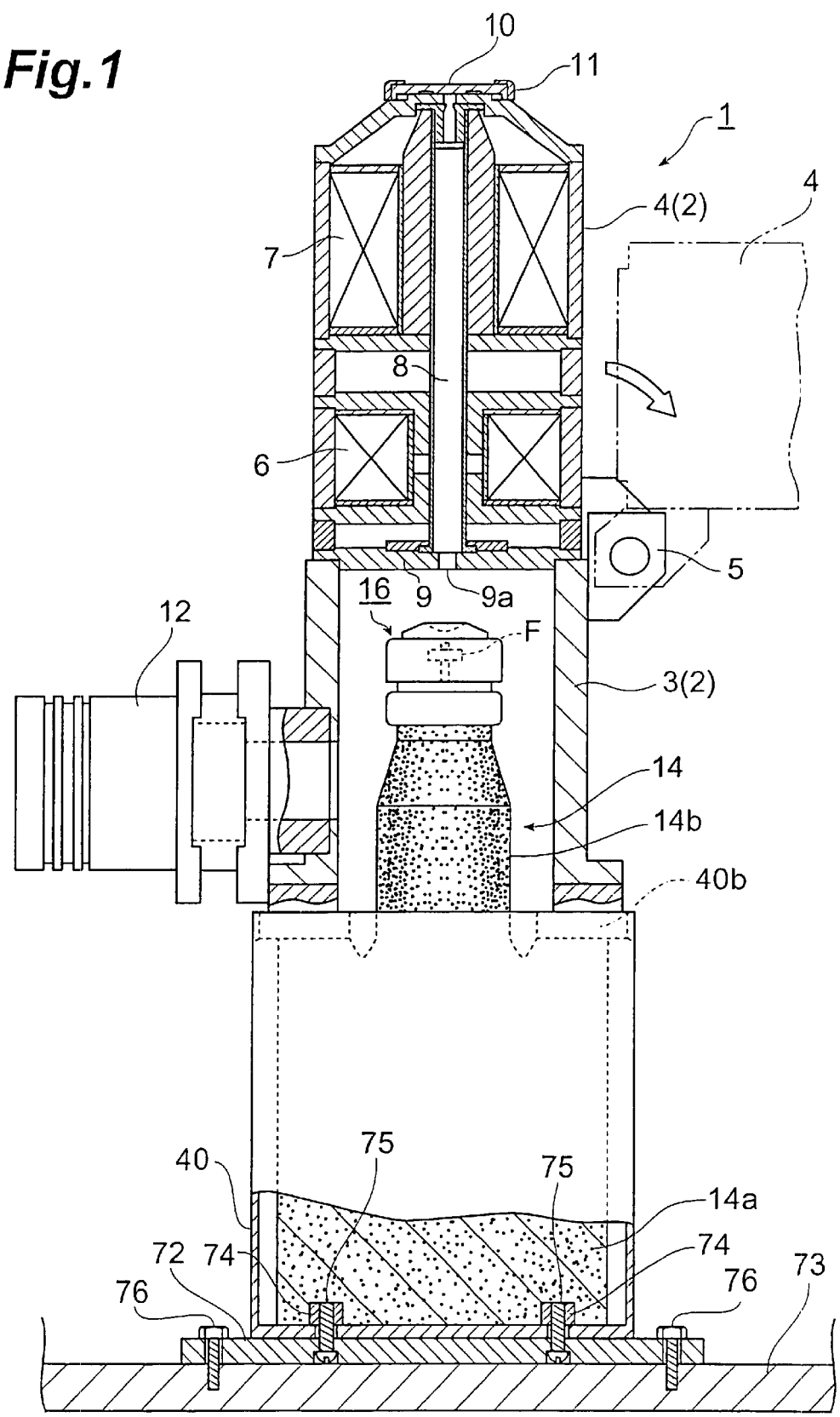
FIG. 1 is a sectional view showing an embodiment of an open type X-ray generating apparatus adapted to the nondestructive inspection apparatus in accordance with the present invention.

As shown in FIG. 1, this X-ray generating apparatus 1 is of an open type and can arbitrarily produce a vacuum state unlike closed types which are disposable, thereby making it possible to replace a filament part F and a target 10 which are consumables. This X-ray generating apparatus 1 has a tubular portion 2 made of stainless steel with a cylindrical form, which attains a vacuum state upon operation. The tubular portion 2 is divided into two parts, i.e., a fixed part 3 and a detachable part 4 which are located on the lower and upper sides, respectively, whereas the detachable part 4 is attached to the fixed part 3 by way of a hinge part 5. Therefore, when the detachable part 4 pivots by way of the hinge part 5 so as to topple sideways, the upper portion of the fixed part 3 can be opened, so as to allow access to the filament part (cathode) F accommodated in the fixed part 3.

Within the detachable part 4, a pair of upper and lower tubular coil parts 6, 7 functioning as an electromagnetic deflection lens are provided, whereas an electron path 8 extends in the longitudinal direction of the tubular portion 2 so as to pass through the centers of the coil parts 6, 7 and is surrounded by the coil parts 6, 7. A disk plate 9 is secured to the lower end of the detachable part 4 so as to close the same, where as an electron inlet hole 9a aligning with the electron path 8 on its lower end side is formed at the center of the disk plate 9.

The upper end of the detachable part 4 is formed into a truncated cone having a top portion to which a disk-shaped target 10, positioned on the upper end side of the electron path 8, for forming an electron transmission type X-ray emission window is attached. The target 10 is made of a member by which an electron generated from the filament F and transmitted through the electron passage 8 is converted into an X-ray, and is accommodated in a detachable rotary cap part 11 while in a state grounded thereto. Therefore, the target 10, which is a consumable, can also be replaced upon removing the cap part 11.

On the other hand, a vacuum pump 12 is secured to the fixed part 3, and is used for attaining a highly vacuum state within the whole tubular portion 2. Namely, since the X-ray generating apparatus 1 is equipped with the vacuum pump 12, the filament part F and target 10, which are consumables, can be replaced.

Here, a mold power unit 14 integrated with an electron gun 16 is secured to the proximal end side of the tubular portion 2. The mold power unit 14 is one molded with an electrically insulating resin (e.g., epoxy resin), and is accommodated within a case 40 made of a metal. The lower end (proximal end) of the fixed part 3 of the tubular portion 2 is firmly secured to an upper plate 40b of the case 40 by screwing or the like in a sealed state.

Figure 2:
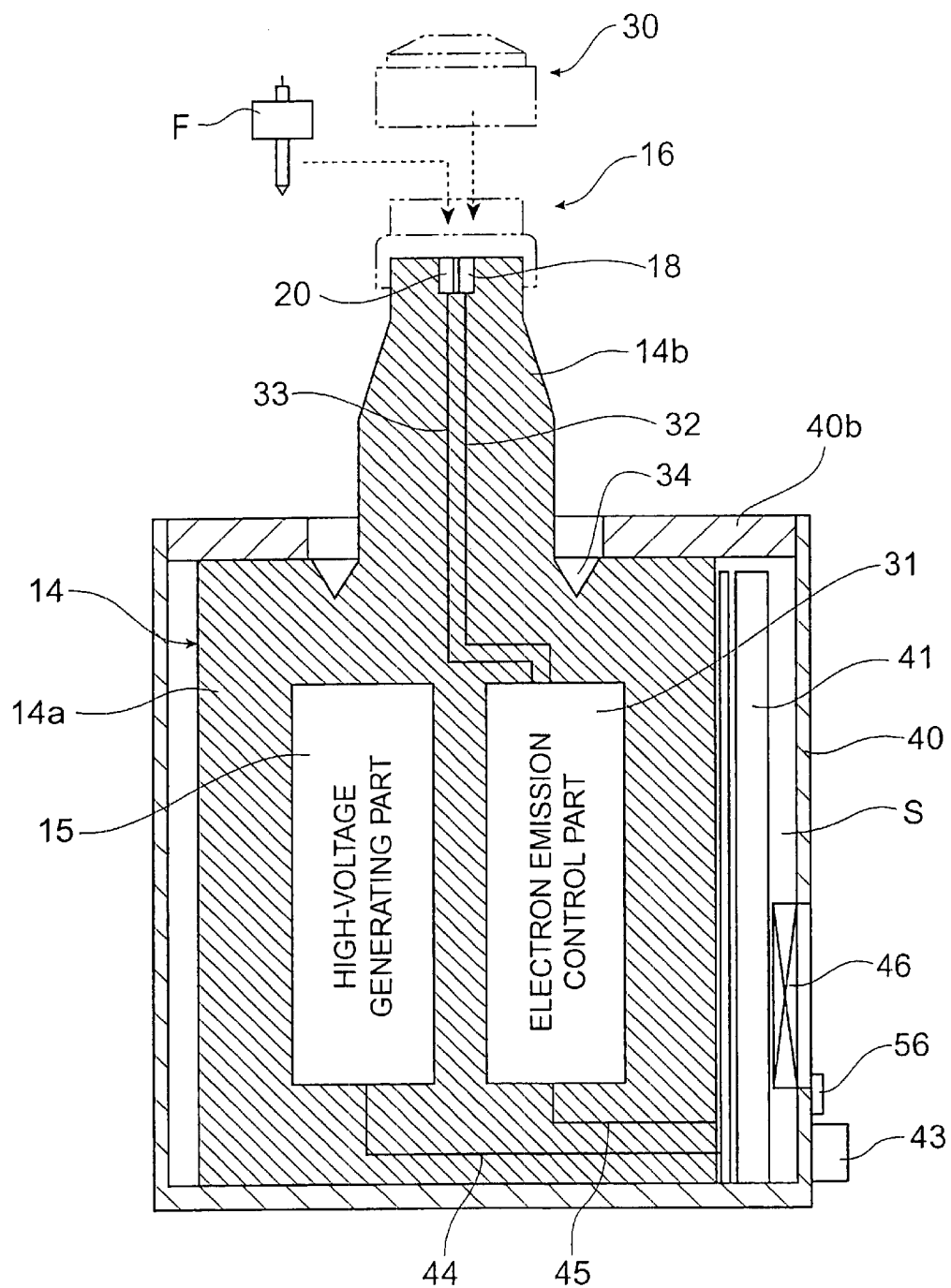
FIG. 2 is a sectional view showing a mold power unit of the X-ray generating apparatus shown in FIG. 1.

As shown in FIG. 2, a high-voltage generating part 15 constituting a transformer generating a high voltage (e.g., a maximum of −160 kV when grounding the target 10) is enclosed within the mold power unit 14. Specifically, the mold power unit 14 comprises a block-shaped power unit body 14a, positioned on the lower side, having a rectangular parallelepiped form; and a columnar neck part 14b projecting upward into the fixed part 3 from the power unit body 14a. Since the high-voltage generating part 15 is a heavy component, it is preferably enclosed within the power unit body 14a, and arranged as low as possible in view of the weight balance of the whole apparatus 1.

Figure 3:
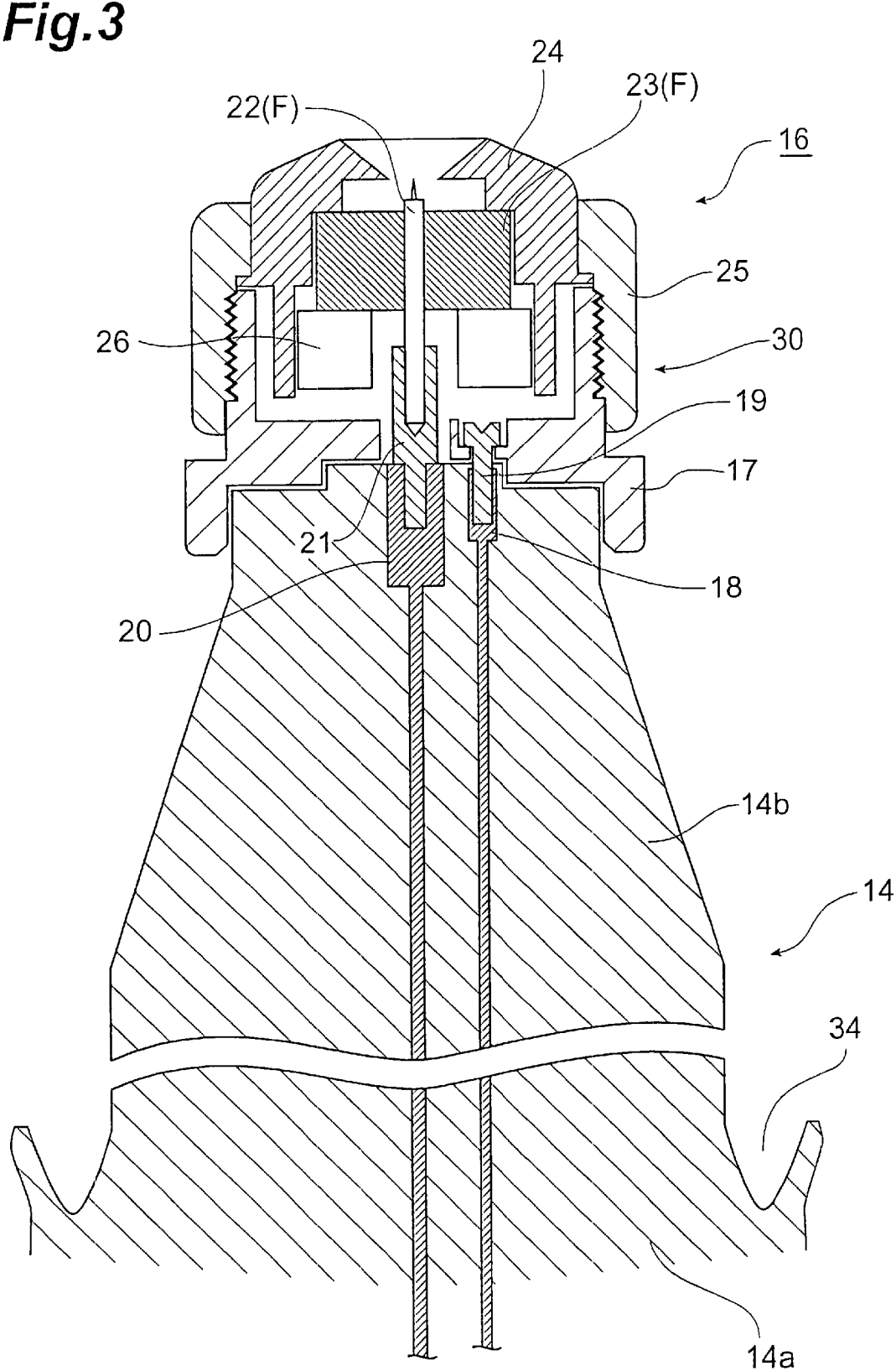
FIG. 3 is a sectional view showing an electron gun of the X-ray generating apparatus shown in FIG. 1.

Attached to the leading end portion of the neck part 14b is the electron gun 16 arranged so as to oppose the target 10 with the electron path 8 interposed there between. As shown in FIG. 3, the electron gun 16 has a grid base 17 to be attached to the neck part 14b, whereas the grid base 17 is fixed, by means of a thread part 19, with respect to a grid terminal 18 embedded in the leading end face of the neck part 14b.

Also, a filament terminal 20 is embedded in the neck part 14b at the leading end face thereof. A heater socket 121 is screwed into the terminal 20, whereas the filament part F is detachably attached to the leading end of the heater socket 21. Here, the filament part F is constituted by a heater pin 22 to be inserted into the heater socket 21 and a heater base 23 for supporting the heater pin 22, whereas the heater pin 22 is freely detachable from the heater socket 21.

Further, the filament part F is covered with a grid cap 24 so as to form a lid, and a grid securing ring 25 is screwed onto the grid base 17, so as to press the grid cap 24 from thereabove. As a result, the heater base 23 of the filament part F accommodated within the grid cap 24 is secured in cooperation with a press ring 26. Thus, the filament part F is configured so as to be replaceable when necessary.

In thus configured electron gun 16, the grid base 17 electrically connected to the grid terminal 18, the grid securing ring 25, and the grid cap 24 constitute a grid part 30. On the other hand, the filament part F electrically connected to the filament terminal 20 by way of the heater socket 21 constitutes a cathode electrode.

Within the power unit body 14a of the mold power unit 14, as shown in FIG. 2, an electron emission control part 31 electrically connected to the high-voltage generating part 15 is enclosed, and controls electron emission timings, tube current, and the like. The electron emission control part 31 is connected to the grid terminal 18 and filament terminal 20 by way of a grid connecting line 32 and a filament connecting line 33, respectively, whereas the connecting lines 32, 33 are enclosed in the neck part 14b since a high voltage is applied to both of them.

Namely, not only the high-voltage generating part 15 but also the grid connecting line 32 feeding electricity to the grid part 30 and the filament connecting line 33 feeding electricity to the filament part F attain a high voltage. Specifically, when the target 10 is grounded, a maximum voltage of −160 kV can be produced in the high-voltage generating part 15. At that time, in a state floated to a high voltage (−160 kV), a voltage of—several hundred V is applied to the grid connecting line 32, whereas a voltage of −2 to −3 V is applied to the filament connecting line 33.

Therefore, when each of such feeder components attaining a high voltage is confined within the electrically insulating resin mold, the degree of freedom in configuration of the high-voltage generating part 15 and the degree of freedom in bending of the lines 32, 33 can be improved remarkably, so as to help the mold power unit 14 reduce its size, thereby making the apparatus itself smaller, which remarkably improves the handling of the apparatus 1.

Further, as shown in FIGS. 1 to 3, the power unit body 14a is provided with a groove part 34 surrounding the base portion of the neck part 14b in an annular fashion. The groove part 34 enhances the creepage distance between the grid base 17 and the case 40, whereby creepage discharge can effectively be prevented from occurring in the surface of the mold power unit 14. On the other hand, the neck part 14b extending from the power unit body 14a into the tubular portion 2 can enhance the creepage distance from the mold power unit 14, whereby creepage discharge can appropriately be prevented from occurring in the surface of the mold power unit 14 when the mold power unit 14 is in a vacuum state.

Figure 4:
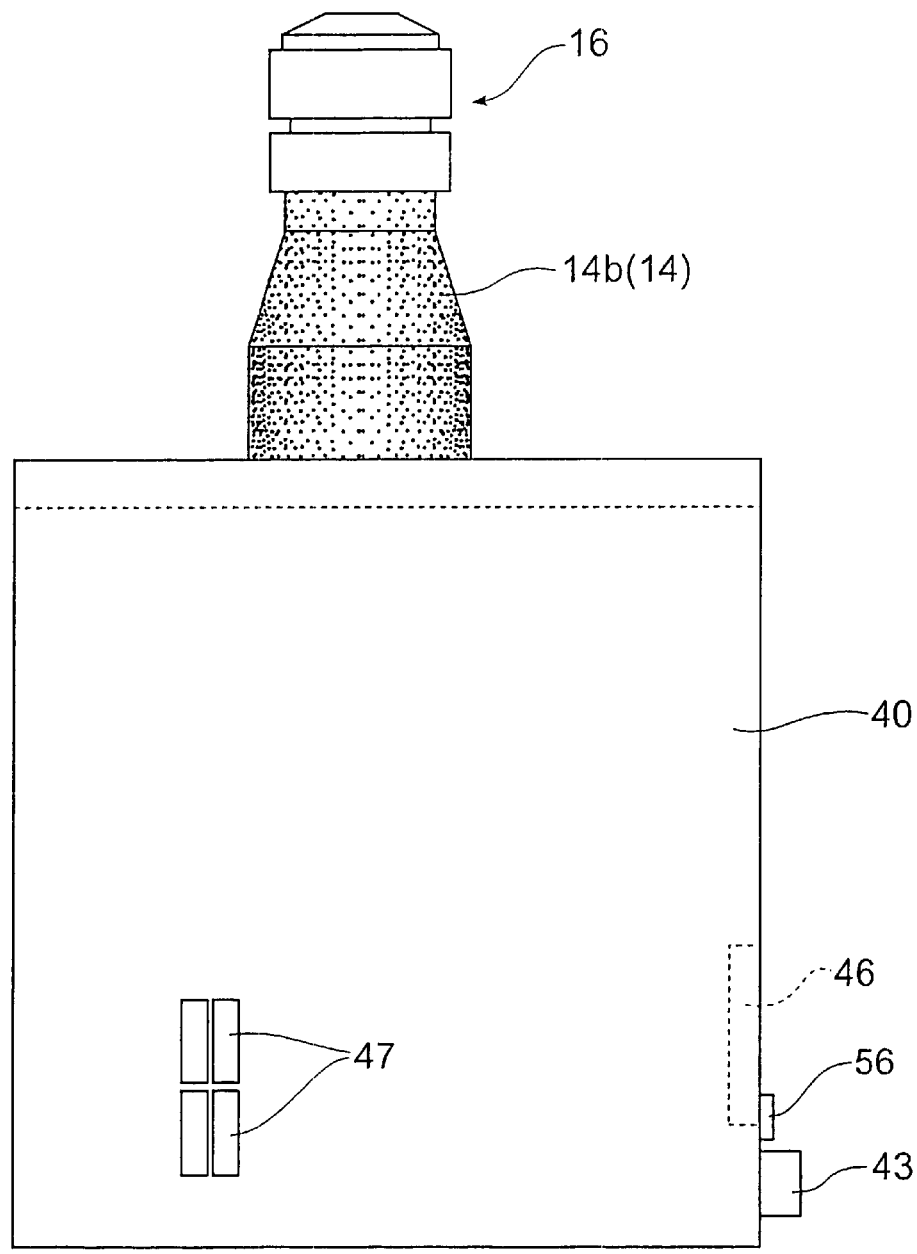
FIG. 4 is a side view showing the appearance of the mold power unit shown in FIG. 2.

Here, as shown in FIGS. 2 and 4, the power unit body 14a is accommodated in the case 40 made of a metal, whereas a space S is provided between the power unit body 14a and the case 40, so that a high-voltage control part 41 is arranged within the space S. A power terminal 43 for connecting with an external power supply is secured to the case 40, whereas the high-voltage control part 41 is connected not only to the power terminal 43, but also to the high-voltage generating part 15 and electron emission control part 31 within the mold power unit 14 by way of lines 44, 45, respectively. Also, according to a control signal from the outside, the high-voltage control part 41 controls a voltage which can be generated in the high-voltage generating part 15 constituting the transformer, such that it ranges from a high voltage (e.g., 160 kV) to a low voltage (0 V). Further, the electron emission control part 31 controls electron emission timings, tube current, and the like. Since the high-voltage control part 41 is disposed in close proximity to the mold power unit 14 whereas the high-voltage control part 41 is stored within the case 40 as such, the handling of the apparatus 1 improves remarkably.

Various electronic components are implemented in such a high-voltage control part 41. Therefore, it is important for each component to be cooled in order to stabilize its operating characteristics. Hence, a cooling fan 46 is attached to the case 40, so that air flows within the space S, whereby the high-voltage control part 41 is forcibly cooled.

Figure 5:
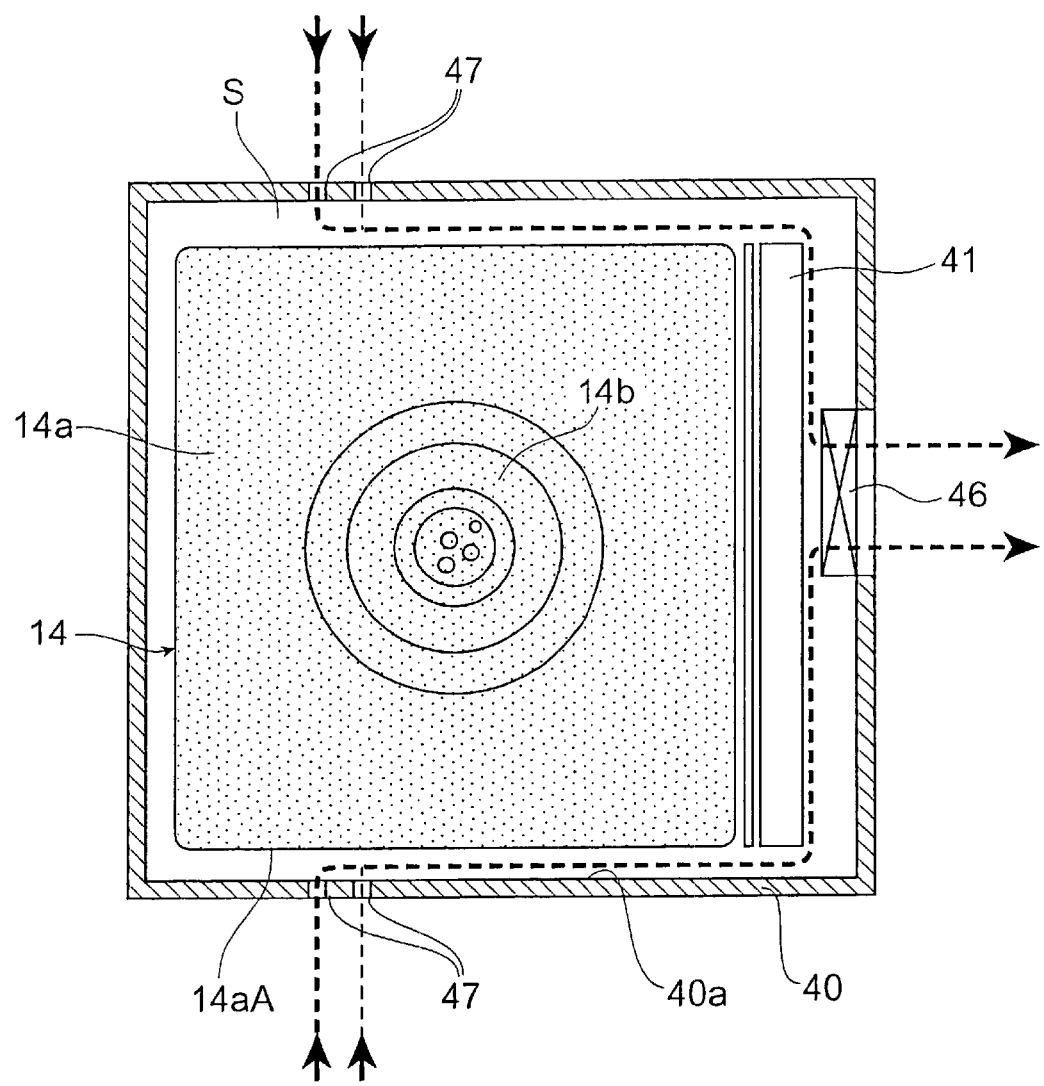
FIG. 5 is a sectional view of a case of the mold power unit shown in FIG. 4.

Further, as shown in FIG. 5, the space S is formed by an inner peripheral face 40a of the case 40 and an outer wall face 14aA of the power unit body 14a so as to surround the outer periphery of the power unit body 14a. A side face of the case 40 is formed with a pair of left and right intake ports 47. As a consequence, the intake ports 47 and the cooling fan 46 cooperate, thereby making it possible to cool not only the high-voltage control part 41, but also the surface of the mold power unit 14. This can stabilize operating characteristics of various components molded within the mold power unit 14, thereby elongating the life of the mold power unit 14. Alternatively, exhaust ports may be referred to with numeral 47, so as to introduce air by use of the cooling fan 46.

Figure 6:
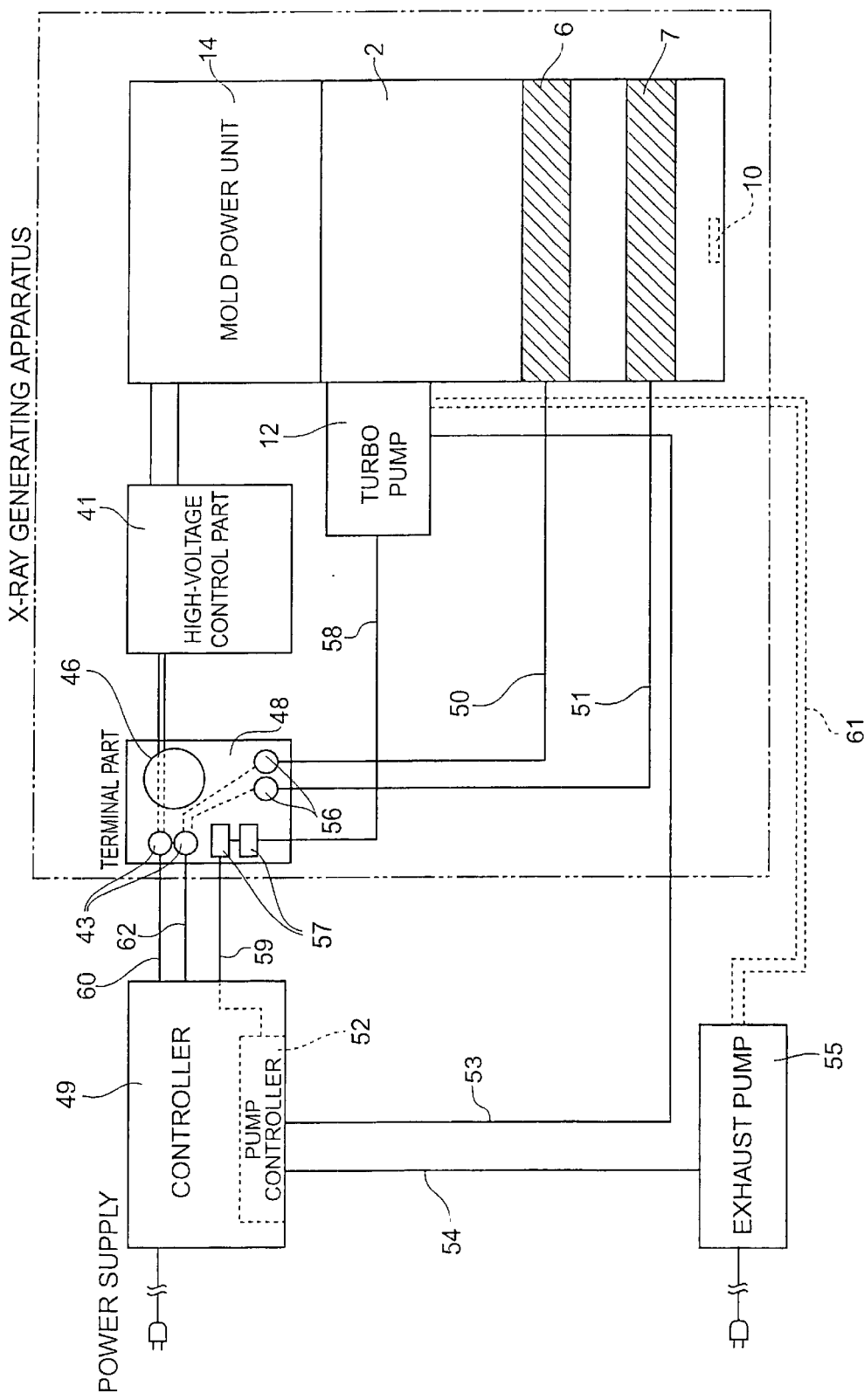
FIG. 6 is a block diagram showing a driving control portion of the X-ray generating apparatus.

In the X-ray generating apparatus 1, as shown in FIG. 6, a terminal part 48 is secured to the case 40. Provided in the terminal part 48 are power terminals 43 to which a controller 49 for connecting with the external power supply is connected by way of detachable lines 60, 62. Here, one terminal 43 is connected to the high-voltage control part 41, whereas the other terminal 43 is connected to coil terminals 56. When such terminals 43 are utilized, the X-ray generating apparatus 1 is appropriately fed with electricity. The terminal part 48 is further provided with the coil terminals 56, to which two detachable coil control lines 50, 51 are connected, respectively, whereas the coil control lines 50, 51 are connected to the coil parts 6, 7, respectively. As a consequence, the feeding of electricity to each of the coil parts 6, 7 is controlled individually.

Therefore, according to the control effected by the controller 49, a power and a control signal are supplied to the high-voltage generating part 15 and electron emission control part 31 of the mold power unit 14, respectively, from the high-voltage control part 41 within the case 40 by way of one terminal 43. Simultaneously therewith, the coil parts 6, 7 are also fed with electricity by way of the lines 50, 51 connected to the other terminal 43. As a result, electrons are emitted from the filament part F with an appropriate acceleration, and are appropriately converged by the controlled coil parts 6, 7, so as to bombard the target 10, whereby X-rays are emitted to the outside.

A pump controller 52 to be utilized when replacing the filament part F and target 10 controls the turbo pump 12 and an exhaust pump 55 by way of lines 53, 54, respectively. Further, the turbo pump 12 and the exhaust pump 55 are connected to each other by way of a pipe 61. Such a configuration of two-stage pump can achieve a high degree of vacuum within the tubular portion 2.

By way of a detachable line 58, a vacuum measuring signal from the turbo pump 12 is fed to one pump terminal 57 of the terminal part 48. By contrast, the other pump terminal 57 is connected to the controller 49 by way of a detachable line 59. As a consequence, the degree of vacuum in the tubular portion 2 is appropriately managed by the controller 49 by way of the lines 58 and 59.

A nondestructive inspection apparatus 70 will now be explained as an example in which the above-mentioned open type X-ray generating apparatus 1 is utilized.

Figure 7:
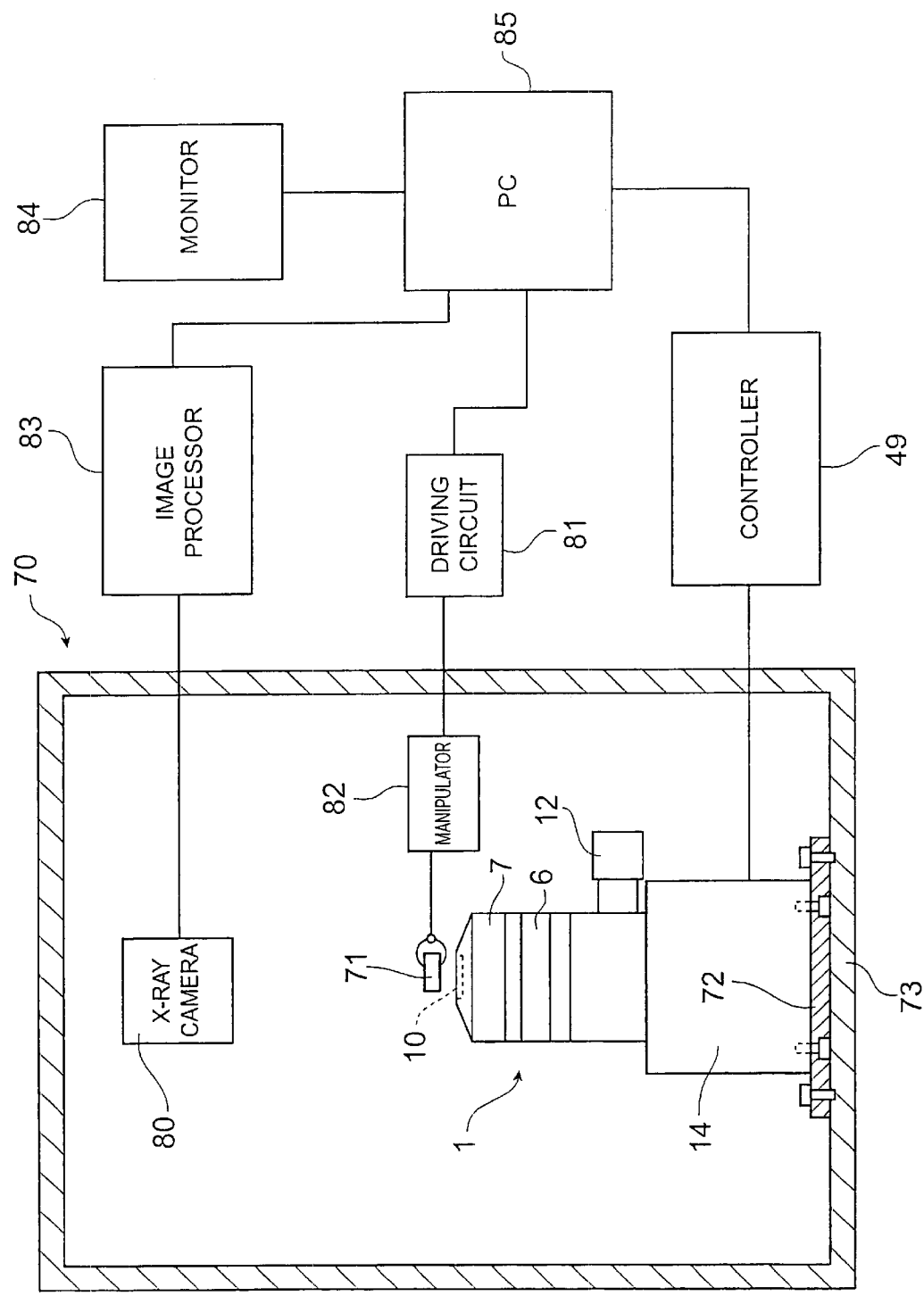
FIG. 7 is a schematic view showing an embodiment of the nondestructive inspection apparatus in accordance with the present invention.

As shown in FIG. 7, the nondestructive inspection apparatus 70 is utilized for inspecting whether a junction part of a lead or the like in an electronic component implemented in a circuit board (object to be inspected) 71 is good or not. The X-ray generating apparatus 1 is installed so as to be secured to the lower part of the nondestructive inspection apparatus 70 while in a state where the target 10 and the heavy mold power unit 14 are located on the upper and lower sides, respectively. Such installation is an arrangement taking the weight balance of the X-ray generating apparatus 1 into consideration, which makes it possible to stably place the X-ray generating apparatus 1, which is hard to topple over. Since the center of gravity of the X-ray generating apparatus 1 is located on the lower side, the X-ray generating apparatus 1 can be maintained in a stable state (see FIG. 1) even in the case where the detachable part 4 is pivoted by way of the hinge part 5 so as to topple sideways when replacing the filament part F.

Also, as can be seen from the configuration mentioned above, the X-ray generating apparatus 1 does not require a high-tension cable which is thick and has a very low degree of freedom in bending. As a result, the X-ray generating apparatus 1 is not required to be placed in the nondestructive inspection apparatus 70 in a suspended state, and can be placed so as to be mounted on the base plate 73, whereby the degree of freedom in its placement can be considered very high.

Further, the X-ray generating apparatus 1 is secured to the base plate 73 of the nondestructive inspection apparatus 70 by way of a vibration absorbing plate 72 made of a rubber material or the like. When the vibration absorbing plate 72 is employed, the X-ray generating apparatus 1 can appropriately be utilized as a microfocus X-ray source.

Specifically, female threads 74 are integrally embedded in the lower face of the power unit body 14a in the mold power unit 14 upon molding as shown in FIG. 1. The female threads 74 and male threads 75 cooperate, so as to secure the vibration absorbing plate 72 to the bottom face of the case 40. Also, the vibration absorbing plate 72 is secured to the base plate 73 of the nondestructive inspection apparatus 70 by installation screws 76. Thus, the X-ray generating apparatus 1 having no high-tension cable can be installed with simple fastening means such as threads alone, which greatly contributes to improving the workability.

In the nondestructive inspection apparatus 70 having thus installed X-ray generating apparatus 1, as shown in FIG. 7, an X-ray camera 80 is placed directly thereabove so as to oppose the target 10, whereby X-rays transmitted through the circuit board 71 are captured by the X-ray camera 80. The circuit board 71 is tilted with an appropriate angle by a manipulator 82 controlled by a driving circuit 81.

Therefore, when the circuit board 71 is swung appropriately, the state of junction of lead parts in electronic components can be observed three-dimensionally. On the other hand, images captured by the X-ray camera 80 are sent to an image processor 83, so as to be displayed on a screen by a monitor 84. The controller 49, driving circuit 81, image processor 83, and monitor 84 are managed by an I/O-capable PC 85.

The above-mentioned embodiment will be summarized as follows:

Preferably, the above-mentioned mold power unit is secured to a base plate by way of a vibration absorbing plate. When such a configuration is employed, the X-ray generating apparatus can be constructed as a microfocus X-ray source which is susceptible to influences of vibrations from the outside.

Preferably, the tubular portion has a fixed part whose proximal end side is secured to the mold power unit, and a detachable part attached to the leading end side of the fixed part. For example, even in the case of an open/close type in which the detachable part topples sideways when replacing the filament part, it is installed on the base plate while in a state where the heavy mold power unit is located on the lower side, whereby the weight balance is hard to lose even when the detachable part is toppled sideways, whereby the stability in installation of the X-ray generating apparatus is easy to maintain.

INDUSTRIAL APPLICABILITY

The present invention relates to a nondestructive inspection apparatus utilizing an open type X-ray generating apparatus making it possible to replace a filament part, which is a consumable, upon vacuum aspiration by use of a pump, and the open type X-ray generating apparatus making the filament part replaceable can stably be placed therein.

I claim:

1. A nondestructive inspection apparatus for irradiating an object to be inspected with an X-ray generated from an open type X-ray generating apparatus which irradiates a target with an electron emitted from an electron gun having a replaceable filament part so as to release said X-ray from said target, and capturing a state of said object to be inspected with an X-ray camera; said open type X-ray generating apparatus comprising a tubular portion, adapted to be vacuumed by a pump, having a coil part therewithin and an electron path surrounded by said coil part; and a mold power unit, secured to a proximal end side of said tubular portion, having a resin-molded high-voltage generating part; wherein said mold power unit is secured to a base plate while in a state where said target disposed on one end side of said tubular portion and said mold power unit disposed on the other end side of said tubular portion are located on the upper and lower sides, respectively.

2. A nondestructive inspection apparatus according to claim 1, wherein said mold power unit is secured to said base plate by way of a vibration absorbing plate.

3. A nondestructive inspection apparatus according to claim 2, wherein said tubular portion has a fixed part having a proximal end side secured to said mold power unit, and a detachable part attached to a leading end side of said fixed part.

4. A nondestructive inspection apparatus according to claim 1, wherein said tubular portion has a fixed part having a proximal end side secured to said mold power unit, and a detachable part attached to a leading end side of said fixed part.

* * * * *